(12) United States Patent
Baileykobayashi et al.

(10) Patent No.: US 10,112,977 B2
(45) Date of Patent: Oct. 30, 2018

(54) PEPTIDE FOR INDUCING MULTINUCLEATION IN CELLS, AND USE THEREFOR

(71) Applicants: Toagosei Co., Ltd., Tokyo (JP); National University Corporation Nagoya University, Aichi (JP)

(72) Inventors: Nahoko Baileykobayashi, Ibaraki (JP); Tetsuhiko Yoshida, Ibaraki (JP); Makoto Sawada, Aichi (JP)

(73) Assignees: Toagosei Co., Ltd., Tokyo (JP); National University Corporation Nagoya University, Aichi (JP)

( * ) Notice: Subject to any disclaimer, the term of this patent is extended or adjusted under 35 U.S.C. 154(b) by 0 days.

(21) Appl. No.: 15/321,247

(22) PCT Filed: Jun. 22, 2015

(86) PCT No.: PCT/JP2015/067920
§ 371 (c)(1),
(2) Date: Dec. 22, 2016

(87) PCT Pub. No.: WO2015/199039
PCT Pub. Date: Dec. 30, 2015

(65) Prior Publication Data
US 2017/0218019 A1   Aug. 3, 2017

(30) Foreign Application Priority Data

Jun. 23, 2014   (JP) .................. 2014-128431

(51) Int. Cl.
| | |
|---|---|
| *A61K 38/08* | (2006.01) |
| *A61K 47/64* | (2017.01) |
| *C07K 7/06* | (2006.01) |
| *A61K 38/00* | (2006.01) |
| *C07K 7/08* | (2006.01) |
| *C07K 14/00* | (2006.01) |
| *C12N 5/09* | (2010.01) |
| *C07K 7/00* | (2006.01) |

(52) U.S. Cl.
CPC ............... *C07K 7/06* (2013.01); *A61K 38/00* (2013.01); *A61K 38/08* (2013.01); *A61K 47/64* (2017.08); *A61K 47/645* (2017.08); *C07K 7/00* (2013.01); *C07K 7/08* (2013.01); *C07K 14/00* (2013.01); *C12N 5/0693* (2013.01); *C07K 2319/10* (2013.01); *C12N 2501/998* (2013.01)

(58) Field of Classification Search
CPC .................................. A61K 38/08; C07K 7/06
See application file for complete search history.

(56) References Cited

U.S. PATENT DOCUMENTS

| | | | | |
|---|---|---|---|---|
| 5,599,708 A | * | 2/1997 | Mundy | ............... C07K 7/08 424/138.1 |
| 2010/0297758 A1 | | 11/2010 | Yoshida et al. | |
| 2012/0122210 A1 | | 5/2012 | Yoshida et al. | |
| 2012/0238023 A1 | | 9/2012 | Eto et al. | |
| 2014/0127815 A1 | | 5/2014 | Eto et al. | |
| 2016/0115449 A1 | | 4/2016 | Eto et al. | |

FOREIGN PATENT DOCUMENTS

| | | |
|---|---|---|
| JP | 2005-523682 | 8/2005 |
| JP | 2006-230413 | 9/2006 |
| WO | WO00/24770 | 5/2000 |
| WO | WO03/031589 | 4/2003 |
| WO | WO2009/093692 | 7/2009 |
| WO | WO2011/013700 | 2/2011 |
| WO | WO2011/034073 | 3/2011 |
| WO | WO2012/157586 | 11/2012 |

OTHER PUBLICATIONS

Lawrence G. Raisz, "Physiology and Pathophysiology of Bone Remodeling" Clinical Chemistry, 45:8(B), 1353-1358, 1999.
Blair et al., "Calcium and Bone Disease", Biofactors, 37(3): 159-167, 2011.
Salisbury, et al., "Centrin-2 is Required for Centriole Duplication in Mammalian Cells", Current Biology, vol. 12, 1287-1292, Aug. 6, 2002.

* cited by examiner

*Primary Examiner* — Jeffrey E. Russel
(74) *Attorney, Agent, or Firm* — Occhiuti & Rohlicek LLP

(57) ABSTRACT

Provided are a synthetic peptide having a multinucleation-inducing activity that can cause multinucleation in a target cell, a multinucleation-inducing agent containing this peptide, and a multinucleation induction method that uses this peptide. The synthetic peptide provided by the present invention is an artificially synthesized peptide that contains (A) a membrane-permeable peptide sequence and (B) a multinucleation-inducing peptide sequence, and that can cause multinucleation in at least one type of eukaryotic cell of human origin or non-human mammal origin. The multinucleation-inducing peptide sequence is constituted of an amino acid sequence given by SEQ ID NO: 1 or SEQ ID NO: 2 or a modified amino acid sequence therefrom.

9 Claims, 3 Drawing Sheets

Specification includes a Sequence Listing.

10 μm

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Cys Pro Asp Gly Ala Lys Ala Arg Cys
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Cys Ser Arg Arg Ser Lys Ser Lys Cys
```

```
1               5

<210> SEQ ID NO 3
<211> LENGTH: 13
<212> TYPE: PRT
<213> ORGANISM: Homo sapiens

<400> SEQUENCE: 3

Lys Lys Arg Thr Leu Arg Lys Asn Asp Arg Lys Lys Arg
1               5                  10

<210> SEQ ID NO 4
<211> LENGTH: 14
<212> TYPE: PRT
<213> ORGANISM: Homo sapiens

<400> SEQUENCE: 4

Arg Ser Arg Lys Tyr Thr Ser Trp Tyr Val Ala Leu Lys Arg
1               5                  10

<210> SEQ ID NO 5
<211> LENGTH: 8
<212> TYPE: PRT
<213> ORGANISM: Avian infectious bronchitis virus

<400> SEQUENCE: 5

Trp Arg Arg Gln Ala Arg Phe Lys
1               5

<210> SEQ ID NO 6
<211> LENGTH: 13
<212> TYPE: PRT
<213> ORGANISM: Human adenovirus

<400> SEQUENCE: 6

Arg Leu Pro Val Arg Arg Arg Arg Arg Val Pro Lys
1               5                  10

<210> SEQ ID NO 7
<211> LENGTH: 11
<212> TYPE: PRT
<213> ORGANISM: Human immunodeficiency virus

<400> SEQUENCE: 7

Tyr Gly Arg Lys Lys Arg Arg Gln Arg Arg Arg
1               5                  10

<210> SEQ ID NO 8
<211> LENGTH: 11
<212> TYPE: PRT
<213> ORGANISM: Artificial sequence
<220> FEATURE:
<223> OTHER INFORMATION: Synthetic peptide

<400> SEQUENCE: 8

Tyr Ala Arg Ala Ala Ala Arg Gln Ala Arg Ala
1               5                  10

<210> SEQ ID NO 9
<211> LENGTH: 16
<212> TYPE: PRT
<213> ORGANISM: Drosophila melanogaster

<400> SEQUENCE: 9

Arg Gln Ile Lys Ile Trp Phe Gln Asn Arg Arg Met Lys Trp Lys Lys
```

```
<210> SEQ ID NO 10
<211> LENGTH: 9
<212> TYPE: PRT
<213> ORGANISM: Artificial sequence
<220> FEATURE:
<223> OTHER INFORMATION: Synthetic peptide

<400> SEQUENCE: 10

Arg Arg Arg Arg Arg Arg Arg Arg Arg
1               5

<210> SEQ ID NO 11
<211> LENGTH: 19
<212> TYPE: PRT
<213> ORGANISM: Homo sapiens

<400> SEQUENCE: 11

Gly Arg Cys Arg Arg Leu Ala Asn Phe Pro Gly Arg Lys Arg Arg
1               5                   10                  15

Arg Arg Arg

<210> SEQ ID NO 12
<211> LENGTH: 24
<212> TYPE: PRT
<213> ORGANISM: Artificial sequence
<220> FEATURE:
<223> OTHER INFORMATION: Synthetic peptide

<400> SEQUENCE: 12

Lys Lys Arg Thr Leu Arg Lys Asn Asp Arg Lys Lys Arg Gly Gly Cys
1               5                   10                  15

Pro Asp Gly Ala Lys Ala Arg Cys
            20

<210> SEQ ID NO 13
<211> LENGTH: 24
<212> TYPE: PRT
<213> ORGANISM: Artificial sequence
<220> FEATURE:
<223> OTHER INFORMATION: Synthetic peptide

<400> SEQUENCE: 13

Lys Lys Arg Thr Leu Arg Lys Asn Asp Arg Lys Lys Arg Gly Gly Cys
1               5                   10                  15

Ser Arg Arg Ser Lys Ser Lys Cys
            20
```

PEPTIDE FOR INDUCING MULTINUCLEATION IN CELLS, AND USE THEREFOR

CROSS REFERENCE TO RELATED APPLICATIONS

This application is a National Stage of International Application No. PCT/JP2015/067920 filed on Jun. 22, 2015, which claims priority to Japanese Application No. 2014-128431 filed on Jun. 23, 2014, the contents of which are hereby incorporated by reference in their entirety.

TECHNICAL FIELD

The present invention relates to a synthetic peptide that can cause multinucleation in a target cell and relates to the use of this synthetic peptide. More particularly, the present invention relates to a multinucleation-inducing agent (pharmaceutical composition) containing this peptide and to a method for inducing multinucleation using this peptide.

BACKGROUND ART

Many of the cells that make up the human body are normally cells that have one nucleus within the individual cell (that is, mononuclear cells), but it is known that some types of cells have a plurality of nuclei within the individual cell (that is, multinuclear cells).

Megakaryocytes and osteoclasts are examples of multinuclear cells that are normally present in an organism (cells that exhibit their normal function while being multinuclear cells). Osteoclasts are multinuclear cells that are differentiated from hematopoietic stem cells and are cells that are responsible for the destruction of old bone tissue (bone resorption) and that participate in bone reconstruction (bone remodeling) and bone growth (Non Patent Literature 1). In addition, they also participate in the regulation of the blood calcium concentration (maintenance of homeostasis) by supplying calcium from hone to the blood through the hone resorption (Non Patent Literature 2). Megakaryocytes are multinuclear cells that are differentiated from hematopoietic stem cells and are cells responsible for platelet production.

Platelets are a blood component (cellular component in the blood) required for blood coagulation and hemostasis and are in great demand in the areas of, for example, leukemia, bone marrow transplantation, and surgery. At the present time, blood products (platelet preparations) acquired by blood donation are frequently used for platelet transfusion to patients that require the administration of platelets. However, transfusable platelets (platelet preparations) have a short retention period (effective period) post-blood collection and their supply is prone to be unstable due to blood donor shortages. As a consequence, art for the production of platelet-producing megakaryocytes from cells (for example, megakaryocyte precursor cells) derived from an organism (for example, the patient) or derived from stem cells, e.g., induced pluripotent stem cells (iPS cells), embryonic stem cells (ES cells), or hematopoietic stem cells, and art for the production of platelets from such megakaryocytes have been anticipated as art crucial for achieving a stable supply of platelets (platelet preparations) that would be independent of blood donation. As art related thereto, for example, Patent Literature 1 describes art for establishing a megakaryocyte precursor cell line that has been immortalized by the forced expressed of certain genes. Patent Literature 2 describes art in which, in order to increase the in vitro production of functional platelets (platelets that maintain their activity, e.g., hemostatic action, in vivo) from megakaryocytes, multinucleation of megakaryocytes is additionally promoted by the forced expression of certain genes.

One characteristic feature of tumor cells (cancer cells) is that cell division is more active than for normal cells and the cell proliferation rate is thus significantly higher. As a consequence, many of the anticancer agents directed to killing tumor cells or suppressing their growth use drugs that inhibit cell division in tumor cells (cancer cells). Alkylating agents, antimetabolites, and microtubule-targeting agents are examples of drugs that inhibit cell division. Alkylating agents inhibit cell division by tumor cells (cancer cells) by a mechanism of action that acts on DNA to crosslink the bases on the double strand with each other; antimetabolites, 5-FU and so forth, inhibit cell division by tumor cells (cancer cells) by a mechanism of action that inhibits DNA synthesis; and microtubule-targeting agents inhibit cell division by tumor cells (cancer cells) by a mechanism of action that inhibits mitosis by inhibiting the polymerization or depolymerization of microtubules. Numerous anticancer agents (antitumor compositions) have been developed to date, but there is still great demand for drugs that are more effective and have a low risk of side effects and for inexpensive drugs that are highly effective. For example, if it were possible to inhibit cell division by tumor cells by artificially and aggressively causing multinucleation of the tumor cells, this could be used as a novel anticancer art (anticancer agent).

Thus, a critical problem for regenerative medicine and cancer treatment is, as in the examples referenced above, to establish an art for artificially producing the multinuclear cells that carry out highly specialized responsibilities in the organism, e.g., megakaryocytes, osteoclasts, and so forth, or to establish an art that realizes the inhibition of cell division based on the multinucleation of tumor cells (cancer cells).

CITATION LIST

Patent Literature

Patent Literature 1: WO 2011/034073
Patent Literature 2: WO 2012/157586
Patent Literature 3: WO 2009/093692

Non Patent Literature

Non Patent Literature 1: Clinical Chemistry, Volume 45 (No. 8), 1999, pp. 1353-1358
Non Patent Literature 2: Biofactors, Volume 37 (No. 3), 2011, pp. 159-167
Non Patent Literature 3: Current Biology, Volume 12, 2002, pp. 1287-1292

SUMMARY OF INVENTION

Thus, the present invention was created taking as a problem the development of an art that could artificially cause the multinucleation of a target cell, and in specific terms an object of the present invention is to provide an artificial peptide that is a relatively short-chain peptide capable of artificial synthesis and that contributes to the goal of inducing the multinucleation of a target cell. An additional object is to provide a multinucleation-inducing agent (pharmaceutical composition) that contains such a peptide. Yet another object is to provide a method for inducing multinucleation of a target cell using such a peptide.

The present inventors intensively advanced research on various peptides that would contribute to the goal of inducing the multinucleation of a target cell. It was surprisingly discovered that the multinucleation of a target cell could be induced or the multinucleation of a target cell could be promoted by supplying to the target cell a peptide synthesized so as to contain the amino acid sequence represented by SEQ ID NO: 1 or 2, and the present invention was achieved based on this discovery. The present inventors have also found that, by inducing tumor cell multinucleation, normal cell division can be inhibited and the proliferation of a target tumor cell (cancer cell) can be stopped or inhibited.

In order to realize the aforementioned objects, the present invention provides an artificially synthesized peptide that, when supplied to a target cell (typically when added to the medium on which the cell is being cultured), characteristically has the capacity to cause the multinucleation of the cell or to promote the multinucleation of the cell (this capacity is also referred to hereafter as a "multinucleation-inducing activity").

That is, the herein disclosed synthetic peptide is an artificially synthesized peptide having a multinucleation-inducing activity for at least one type of eukaryotic cell and characteristically having, in the peptide chairs thereof the following amino acid sequence (A) and amino acid sequence (B):

(A) an amino acid sequence that constitutes a membrane-permeable peptide sequence; and (B) an amino acid sequence given by either CPDGA-KARC (SEQ ID NO: 1) or CSRRSKSKC (SEQ ID NO: 2) constituting multinucleation-inducing peptide sequences that have a multinucleation-inducing activity on at least one type of eukaryotic cell, or a modified amino acid sequence that is obtained by substitution, deletion, and/or addition of one or a plurality of amino acid residues in the aforementioned amino acid sequences and that constitutes a multinucleation-inducing peptide sequence having a multinucleation-inducing activity on at least one type of eukaryotic cell.

In this Description, "multinucleation-inducing synthetic peptide" is also used to refer to the synthetic peptide containing a multinucleation-inducing peptide sequence and a membrane-permeable peptide sequence (including peptides composed of a modified amino acid sequence as described above), i.e., synthetic peptides having a multinucleation-inducing activity.

The herein disclosed multinucleation-inducing synthetic peptide characteristically has the multinucleation-inducing peptide sequence given by (B) above in the peptide chain thereof. As a consequence of this, multinucleation can be induced in a target cell, or multinucleation can be promoted in a target cell, by supplying this synthetic peptide to the target cell (typically in the medium in which the cell is cultured). This multinucleation-inducing synthetic peptide also has a membrane-permeable peptide sequence as shown in (A) above in the peptide chain thereof, and as a consequence, by supplying this peptide to a target cell (typically in the medium on which the cell is cultured), the subject multinucleation-inducing peptide sequence can be very efficiently transported into the interior of the eukaryotic cell from outside the cell (outer side of the cell membrane). In addition, because multinucleation can be induced in the target cell by the supply of a synthetic peptide, the introduction of foreign genes into the genome that could be caused by gene transfer is not a concern. The herein disclosed art thus makes possible the realization of the induction of multinucleation in a target cell using a simple and convenient treatment method, i.e., the supply of the multinucleation-inducing synthetic peptide to the target cell (typically in the medium on which the cell is cultured).

The herein disclosed multinucleation-inducing synthetic peptide can also be easily produced artificially by chemical synthesis (or biosynthesis). When such a multinucleation-inducing synthetic peptide is used, multinucleation can be brought about in the target cell (typically as an alternative to humoral factors and so forth) without the use of large amounts of expensive humoral factors and so forth, typically cytokines, and as a consequence multinucleation induction in the target cell can be realized at low cost. The herein disclosed multinucleation-inducing synthetic peptide has a simple structure (typically a linear peptide chain) and has a high structural stability and as a consequence has excellent handling properties.

In a preferred aspect of the herein disclosed synthetic peptide (multinucleation-inducing synthetic peptide), the amino acid sequence constituting the aforementioned membrane-permeable peptide sequence (A) is characteristically any amino acid sequence selected from SEQ ID NOs: 3 to 11 or a modified amino acid sequence constituting a membrane permeable peptide sequence and obtained by substitution, deletion, and/or addition of one or a plurality of amino acid residues in the aforementioned amino acid sequences.

The amino acid sequences given by SEQ ID NOs: 3 to 11 are all typical examples of amino acid sequences that constitute a membrane-permeable peptide and can be favorably used as the membrane-permeable peptide sequence indicated in (A). Among these, the use is preferred of any of the amino acid sequences known as a nucleolar localization signal (NoLS) (typically the amino acid sequences given by SEQ ID NOs: 3 to 6), which is a signal sequence that causes the localization of protein to the nucleolus within the nucleus. In particular, a membrane-permeable peptide sequence constituted of the amino acid sequence given by SEQ ID NO: 3 is a typical example of an NoLS and is particularly preferred from the standpoint of the efficiency of transport of the multinucleation-inducing peptide sequence into a cell.

A synthetic peptide according to a herein disclosed preferred aspect (multinucleation-inducing synthetic peptide) is characterized in that the overall amino acid sequence constituting the peptide chain is not more than 30. A peptide composed of such a short peptide chain is easily chemically synthesized, has a relatively inexpensive cost of production, and has excellent handling properties. Due to this, it can be favorably used, for example, as a component of a multinucleation-inducing agent.

In a preferred aspect of the herein disclosed synthetic peptide (multinucleation-inducing synthetic peptide), it characteristically has either of the following amino acid sequences:

```
                                        (SEQ ID NO: 12)
    KKRTLRKNDRKKRGGCPDGAKARC;
    and
                                        (SEQ ID NO: 13)
    KKRTLRKNDRKKRGGCSRRSKSKC.
```

Such a multinucleation-inducing synthetic peptide is favorable for use to induce multinucleation in cells of human origin or cells of non-human mammal origin.

In another aspect, the present invention provides a multinucleation-inducing agent (pharmaceutical composition)

used to induce multinucleation in at least one type of eukaryotic cell, wherein the multinucleation-inducing agent contains the multinucleation-inducing synthetic peptide according to any of the herein disclosed aspects and a pharmaceutically acceptable carrier (for example, at least one substrate or liquid medium, e.g., physiological saline or various buffers, that contributes to enhancing the stability of this peptide).

Because a composition with the instant constitution contains a synthetic peptide (the multinucleation-inducing synthetic peptide) having the aforementioned multinucleation-inducing peptide sequence, the multinucleation of a target cell can be induced (or multinucleation can be promoted) by supplying this composition (the multinucleation-inducing synthetic peptide) to the target cell (typically in the medium on which the cell is cultured).

The herein disclosed multinucleation-inducing agent is advantageously used for the purpose of causing a tumor cell of human origin or non-human mammal origin to undergo multinucleation. Malignant tumor cells (cancer cells), for example, squamous cell carcinoma cells and adenocarcinoma are particularly preferred target cells.

The induction of multinucleation in a tumor cell by the herein disclosed multinucleation-inducing agent serves to inhibit cell division by the cell that has been multinucleated (multinucleated cell) and as a result can prevent or inhibit proliferation of the tumor cell. In other words, the herein disclosed multinucleation-inducing agent can be used as a composition for inhibiting the proliferation of a tumor cell of human origin or non-human mammal origin. That is, the herein disclosed multinucleation-inducing agent can be advantageously used as an antitumor composition (anticancer agent) for enabling the expression of an antitumor effect on a target tumor cell.

In another aspect, the present invention provides a method for causing multinucleation in at least one type of eukaryotic cell in vivo or in vitro.

A preferred aspect is a method for inducing multinucleation of at least one type of eukaryotic cell in vitro, wherein the multinucleation induction method comprises preparing in vitro a cell culture that contains a target cell; supplying a multinucleation-inducing synthetic peptide (or a multinucleation-inducing agent containing this synthetic peptide) according to any of the herein disclosed aspects at least once to the cell culture; and culturing the cell culture to which the peptide has been supplied.

Using this multinucleation induction method, multinucleation can be efficiently induced (or multinucleation can be efficiently promoted) in a target cell (or in tissue containing this cell) by a simple and convenient method that uses a synthetic peptide with the simple constitution as described above (or a multinucleation-inducing agent that contains this synthetic peptide) as a multinucleation-inducing synthetic peptide factor.

The herein disclosed multinucleation induction method can be advantageously carried out with the goal of inducing the multinucleation of a tumor cell of human origin or non-human mammal origin. Using the herein disclosed multinucleation induction method, the induction of multinucleation can be readily realized in particular in malignant tumor cells (cancer cells), for example, cells of squamous cell carcinoma origin and cells of adenocarcinoma origin. That is, the herein disclosed multinucleation induction method can inhibit cell division in tumor cells of human origin ear non-human mammal origin and can prevent or inhibit the proliferation of these cells. Accordingly, the herein disclosed multinucleation induction method can be used as a method for treating tumors (cancers).

The herein disclosed multinucleation-inducing synthetic peptide (or multinucleation-inducing agent containing this peptide) can be advantageously used for the purpose of inducing the multinucleation of a multinuclear cell or a pre-multinuclear cell prior to multinucleation (for example, a megakaryoblast prior to multinucleation or an osteoclast precursor cell prior to multinucleation). This makes it possible to realize an increase in the number of nuclei in a multinuclear cell (promotion of multinucleation) and to realize the preparation (production) of a multinuclear cell (for example, a megakaryocyte, osteoclast, and so forth).

In other words, a multinuclear cell in which multinucleation has been satisfactorily induced (promoted) (for example, a megakaryocyte, osteoclast, and so forth) can be prepared (produced) by the execution of a multinucleation induction method that is characterized by supplying the herein disclosed multinucleation-inducing synthetic peptide to a target multinuclear cell or target pre-multinuclear cell prior to multinucleation. The use of this method is preferred because it makes possible the preparation (production) of multinuclear cells by a simple and convenient method, i.e., the use as a multinucleation-inducing factor of the synthetic peptide with the simple constitution as described above (that is, a multinucleation-inducing agent containing this synthetic peptide).

Alternatively, multinuclear cells (for example, megakaryocytes, osteoclasts, and so forth) prepared (produced) by the herein disclosed method (typically an in vitro multinucleation induction method), cells produced from these multinuclear cells (for example, platelets), and biosynthetic products produced from these multinuclear cells (tor example, physiologically active substances such as secreted proteins and hormones) can be used as a cell resource for use in regenerative medicine. For example, megakaryocytes prepared (produced) by the herein disclosed method (i.e., megakaryocytes in which multinucleation has satisfactorily advanced) can be used as a cultured cell line for producing cells for transplantation (typically for hone marrow transplantation and for the in vitro production of platelets. In addition, platelet preparations (blood preparations) can be produced using the platelets produced from megakaryocytes prepared (produced) using the herein disclosed method. This makes it possible to realize a platelet supply (platelet preparation) that is independent of blood donation.

DESCRIPTION OF EMBODIMENTS

Preferred embodiments of the present invention are described below. In addition to those matters that are particularly described in this Description (for example, the primary structure and chain length of the herein disclosed synthetic peptide), those matters required for the execution of the present invention but not particularly described in this Description (for example, methods for the chemical synthesis of the peptide, cell culture techniques, general matters relating to the preparation of a pharmaceutical composition having a peptide as a component) can be understood as design matters for the individual skilled in the art based on the conventional art in the fields of, for example, cell engineering, physiology, medicine, pharmacy, organic chemistry, biochemistry, genetic engineering, protein engineering, molecular biology, and genetics. The present invention can be implemented based on the contents disclosed in this Description and the common general technical knowledge in these fields. Depending on the case, the amino acids are given by one-letter symbols in conformity with the amino acid nomenclature given in the IUPAC-IUB guidelines (however, the three-letter designations are used in the sequence listings).

The content of each literature cited in this Description is incorporated in its entirety in this Description by reference.

In this Description, "synthetic peptide" refers to a peptide fragment whose peptide chain as such does not exist independently in a stable manner in nature, but rather is produced by artificial chemical synthesis or biosynthesis (that is, production based on genetic engineering) and can exist in a stable manner in a prescribed composition (for example, a multinucleation-inducing agent that can induce multinucleation in a target cell).

Also in this Description, "peptide" is a term that indicates an amino acid polymer that has a plurality of peptide bonds and, while there is no limitation on the number of amino acid residues that may be present in the peptide chain, this term typically refers to a relatively low molecular weight wherein the total number of amino acid residues is not more than about 100 (preferably not more than 50 and more preferably not more than 30).

Also in this Description, "amino acid residue" is a term that includes, unless specifically indicated otherwise, the N-terminal amino acid and C-terminal amino acid of the peptide chain.

The amino acid sequences described in this Description always have the N-terminal side for the left side and the C-terminal side for the right side.

In this Description, a "modified amino acid sequence" refers, with respect to a particular amino acid sequence, to an amino acid sequence formed by the substitution, deletion, and/or addition (insertion) of 1 or a plurality (typically 1 to 5, for example, 1, 2, or 3) of amino acid residues, but without the loss of the function exhibited by be particular amino acid sequence (for example, the multinucleation-inducing activity possessed by the aforementioned multinucleation-inducing synthetic peptide or the transport function from cell exterior to the cell interior possessed by the membrane-permeable peptide). Typical examples that are encompassed by the modified amino acid sequences referenced by this Description include, for example, the following: sequences produced by what is known as conservative amino acid replacement, in which conservative substitution by 1 or a plurality (typically 2 or 3) of amino acid residues is carried out (for example, a sequence in which a basic amino acid residue is replaced by another basic amino acid residue: for example, exchange between the lysine residue and the arginine residue), and sequences obtained by the addition (insertion) to a particular amino acid sequence or deletion from a particular amino acid sequence of 1 or a plurality (typically about 1 to 5, for example, 1, 2, or 3) of amino acid residues. Accordingly, the herein disclosed multinucleation-inducing synthetic peptide encompasses synthetic peptides constituted of an amino acid sequence that is the same as an amino acid sequence according to the SEQ ID NOs, but also encompasses synthetic peptides constituted of an amino acid sequence obtained by the substitution (for example, the aforementioned conservative amino acid replacement), deletion, and/or addition of 1 or a plurality of amino acid residues in an amino acid sequence given by a SEQ ID NO, wherein these synthetic peptides exhibit the same or a similar multinucleation-inducing activity.

In this Description, "tumor" is a term that is to be broadly construed and refers to tumors in general (typically malignant tumors) including carcinomas, sarcomas, and lesions of the blood and haematopoietic tissues (leukemias, lymphomas, and so forth). Moreover, "tumor cell" refers to the cells that form such tumors. This typically refers to cells (so-called cancerous cells) that have engaged in abnormal growth independently of the surrounding normal tissue. Therefore, unless specifically indicated otherwise, a cell that is not a normal cell and that is classified as a tumor cell (cancer cell) is referred to as a tumor cell regardless of the origin and properties of the cell. The tumor cells referenced herein can include the cells making up epithelial tumors (squamous cell carcinoma, adenocarcinoma, and so forth), nonepithelial tumors (various sarcomas, osteosarcomas, and so forth), various cytomas (neuroblastomas, retinoblastomas, and so forth), lymphomas, melanomas, and so forth.

A "multinuclear cell" in this Description is a term designating a cell that is present in the organism as a cell normally having a plurality of nuclei (typically at least 2, for example, at least 4), i.e., is a term designating a cell whose normal form in the organism is a form having a plurality of nuclei. Examples here are megakaryocytes, osteoclasts, skeletal muscle cells, the syncytiotrophoblasts present in placental villi, and foreign body giant cells, which are phagocytes of macrophage origin.

Also in this Description, a "pre-multinuclear cell prior to multinucleation" refers to a multinuclear cell that has not undergone polyploidization and typically refers to a mononuclear cell (including cells having 2 nuclei during mitosis (M phase)). Specific examples of pre-multinuclear cells prior to multinucleation are megakaryocyte precursor cells (megakaryoblasts) and precursor cells for osteoclasts (osteoclast precursor cells).

In this Description, "induction of multinucleation" and "promotion of multinucleation" refer to a relative increase in the number of nuclei within a cell as compared to the cell prior to the induction (promotion) of multinucleation. For example, obtaining a cell having at least 2 nuclei (typically at least 4, for example, at least 8) from a mononuclear cell and increasing the number of nuclei in a multinuclear cell can be referred to as the induction (promotion) of multinucleation. Moreover, since typically the ploidy increases as the number of nuclei in a cell increases, the "induction (promotion) of multinucleation" can also be understood as bringing about an increase in the ploidy relative to that of the cell prior to the induction of multinucleation. For example, the induction (promotion) of multinucleation can also refer to the application of the present invention to a cell having a chromosome count of 2N to obtain a cell having a chromosome count of at least 4N (typically at least 8N, for example, at least 16N).

The herein disclosed multinucleation-inducing synthetic peptide is a synthetic peptide discovered for the first time by the present inventors to exhibit the action—when supplied to a cell culture (typically by addition to the medium in which the cells are being cultured) of a particular eukaryotic cell (typically a cell of human origin, or non-human mammal origin, or avian origin, or from some other animal) of being able to induce the multinucleation of the cell or promote the multinucleation of the cell (i.e., has the ability to increase the number of nuclei in the cell), i.e., it has a multinucleation-inducing activity (that is, this synthetic peptide is a multinucleation-inducing synthetic peptide). In addition, the herein disclosed multinucleation-inducing agent is a composition (pharmaceutical composition) that can induce (promote) the multinucleation of a target cell and that characteristically contains at least one type of the aforementioned multinucleation-inducing synthetic peptide as an effective component (that is, a substance that participates in the induction of multinucleation in a target cell).

As indicated above, the herein disclosed multinucleation-inducing synthetic peptide has, as partial amino acid sequences (peptide motifs), the aforementioned amino acid sequence specified by (A) that constitutes a membrane-permeable peptide sequence and the aforementioned amino acid sequence specified by (B) constitutes a multinucleation-inducing peptide sequence.

The multinucleation-inducing peptide sequence (B) in the multinucleation-inducing synthetic peptide is a sequence that has a multinucleation-inducing activity and, through its combination with the membrane-permeable peptide sequence (A), is an amino acid sequence (peptide motif) that, as discovered by the present inventors, enables the construction of a peptide that has an excellent multinucleation-inducing activity. In specific terms, this multinucleation-inducing peptide sequence is either of the following amino acid sequences:

CPDGAKARC; (SEQ ID NO: 1)
and

CSRRSKSKC, (SEQ ID NO: 2)

or is composed of a modified amino acid sequence therefrom. The amino acid sequences given by SEQ ID NO: 1 and SEQ ID NO: 2 are artificial amino acid sequences of a total of 9 amino acid residues and were obtained—using the amino acid sequence data obtained when the present inventors carried out their own translation of RNA sequences that constituted siRNA for centrin 2 of human origin—by a reverse rearrangement such that the first, second, third, fourth, fifth, sixth, seventh, eighth, and ninth amino acid residues from the N-terminal side became, respectively, the first, second, third, fourth, fifth, sixth, seventh, eighth, and ninth amino acid residues from the C-terminal side.

This centrin is a centrosome-associated protein that is present in the centrosome of eukaryotes and, as a constituent protein of the centriole, is involved with centriole replication and microtubule cleavage, and centrin 2 is a protein belonging to the centrin family (typically, centrin 1, centrin 2, centrin 3, and so forth) (Non Patent Literature 3).

Any amino acid sequence that constitutes a membrane-permeable peptide that can pass through the cell membrane and/or the nuclear membrane can be used without particular limitation for the membrane-permeable peptide sequence (A) of the herein disclosed multinucleation-inducing synthetic peptide. Numerous amino acid sequences that can satisfactorily function as membrane-permeable peptides (that is, membrane-permeable peptide sequences) are known, but in particular an amino acid sequence (including modified amino acid sequences) associated with a nucleolar localization signal (NoLS) is preferred for the amino acid sequence of the membrane-permeable peptide sequence of the multinucleation-inducing synthetic peptide. Advantageous examples a NoLS-associated membrane-permeable peptide sequences and other membrane-permeable peptide sequences including modified amino acid sequences) are given in SEQ ID NOs: 3 to 11. The specifics are given in the following.

Thus, the amino acid sequence in SEQ ID NO: 3 corresponds to an NoLS composed of a total of 13 amino acid residues from the 491st amino acid residue to the 503rd amino acid residue of the LIM kinase 2 present in human endothelial cells, which is a type of protein kinase involved with intracellular signal transduction.

The amino acid sequence in SEQ ID NO: 4 corresponds to an NoLS composed of a total of 14 amino acid residues derived from basic fibroblast growth factor (FGF2).

The amino acid sequence in SEQ ID NO: 5 corresponds to an NoLS composed of a total of 8 amino acid residues contained in the nucleocapsid (N) protein of avian infectious bronchitis virus (IBV).

The amino acid sequence in SEQ ID NO: 6 corresponds to an NoLS composed of a total of 13 amino acid residues derived from pre-terminal protein (PTP) 1 and PTP 2 of adenovirus.

The amino acid sequence of SEQ ID NO: 7 corresponds to a membrane-permeable peptide sequence composed of a total of 11 amino acid residues derived from the protein transduction domain contained in TAT of human immunodeficiency virus (HIV).

The amino acid sequence of SEQ ID NO: 8 corresponds to a membrane-permeable peptide sequence composed of a total of 11 amino acid residues of a modified-TAT protein transduction domain (PTD4).

The amino acid sequence of SEQ ID NO: 9 corresponds to a membrane-permeable peptide sequence composed of a total of 16 amino acid residues derived from ANT of Antennapedia, a *Drosophila* mutant.

The amino acid sequence of SEQ ID NO: 10 corresponds to a membrane-permeable peptide sequence composed of a total of 9 connected arginine residues functioning as a polyarginine.

The amino acid sequence of SEQ ID NO: 11 corresponds to a membrane-permeable peptide sequence composed of a total of 19 amino acid residues derived from myoblast determination (MyoD) family inhibitor domain-containing protein.

The membrane-permeable peptide sequences given in the sequence listings are given entirely by way of example, and usable peptide sequences are not limited to these. Various membrane-permeable peptide sequences usable for the execution of the present invention are described in numerous publications that had been published at the time of filing of this application. The amino acid sequences of these membrane-permeable peptide sequences can be readily acquired by common search means.

In particular, the amino acid sequence shown in SEQ ID NO: 3, which is also described in Patent Literature 3, is preferred (including modified amino acid sequences) for the membrane-permeable peptide sequence. A synthetic peptide having a high multinucleation-inducing activity can be obtained by combining the membrane-permeable peptide sequence given in SEQ ID NO: 3 with a multinucleation-inducing peptide sequence as described above.

The peptide chain (amino acid sequence) of the herein disclosed multinucleation-inducing synthetic peptide can be constructed by combining a multinucleation-inducing peptide sequence (B) as described above with a membrane-permeable peptide sequence (A) as appropriate. In relational terms, either of the multinucleation-inducing peptide sequence and membrane-permeable peptide sequence may be located at the C-terminal side (N-terminal side). In addition, the multinucleation-inducing peptide sequence is preferably located adjacent to the membrane-permeable peptide sequence. That is, either an amino acid residue not belonging to these two sequences is not present between the multinucleation-inducing peptide sequence and the membrane-permeable peptide sequence, or, if present, the number of such residues is preferably about 1 to 3. For example, 1 or a plurality (typically 1, 2, or 3) of amino acid residues (for example, 1 or a plurality of glycine (G) residues) that function as a linker may be incorporated between the multinucleation-inducing peptide sequence and the membrane-permeable peptide sequence.

The herein disclosed multinucleation-inducing synthetic peptide is preferably one in which at least one of the amino acid residues is amidated. The amidation of the carboxyl group in an amino acid residue (typically the C-terminal amino acid residue of the peptide chain) can improve the structural stability (for example, the resistance to protease) of a synthetic peptide.

In addition, the herein disclosed multinucleation-inducing synthetic peptide may contain, insofar as the multinucleation-inducing activity is not impaired, a sequence (amino acid residue) portion other than the amino acid sequences that constitute the multinucleation-inducing peptide sequence and membrane-permeable peptide sequence. While there is no particular limitation thereon, this partial amino acid sequence is preferably a sequence that can maintain the three-dimensional shape t typically a linear shape) of the multinucleation-inducing synthetic peptide sequence and membrane-permeable peptide sequence portion. The total number of amino acid residues constituting the peptide chain of the multinucleation-inducing synthetic peptide is suitably not more than 100, desirably not more than 60, and preferably not more than 50. For example, a synthetic peptide with not more than 30 is particularly preferred.

Such a short-chain peptide is easily chemically synthesized and a multinucleation-inducing synthetic peptide can then be inexpensively provided. There are no particular limitations on the conformation (steric structure) of the peptide as long as it can exhibit a multinucleation-inducing activity that induces the multinucleation of a target eukaryotic cell in the environment of use (in vitro or in vivo). However, a linear or helical shape is preferred from the standpoint of resistance to becoming an immunogen (antigen). It is difficult for a peptide with such a shape to constitute an epitope. Viewed from this perspective, the multinucleation-inducing synthetic peptide used in the multinucleation-inducing agent is suitably linear and has a relatively low molecular weight (typically not more than 50 amino acid residues and particularly preferably not more than 30 amino acid residues).

The proportion taken up by the multinucleation-inducing peptide sequence and membrane-permeable peptide sequence in the overall amino acid sequence (peptide chain) (that is, the number % tier the number of amino acid residues that constitute the multinucleation-inducing peptide sequence and membrane-permeable peptide sequence with reference to the total number of amino acid residues that constitute the peptide chain of the multinucleation-inducing synthetic peptide) is not particularly limited insofar as the multinucleation-inducing activity of inducing multinucleation in a target cell is not impaired; however, this proportion is desirably at least about 60%, preferably at least 80%, and particularly preferably at least 90%. A peptide composed of the multinucleation-inducing peptide sequence and the membrane-permeable peptide sequence (that is, these sequences are 100% of the overall amino acid sequence, or, when a linker of 1 to several amino acid residues is present, these sequences account for everything other than the linker) is a preferred embodiment.

All of the amino acid residues in the multinucleation-inducing synthetic peptide of the present invention are preferably L-amino acids, but, insofar as the multinucleation-inducing activity of inducing the multinucleation of a target eukaryotic cell is not impaired, all or a portion of the amino acid residues may be replaced by D-amino acids.

A preferred embodiment of the herein disclosed multinucleation-inducing synthetic peptide particularly preferably contains either amino acid sequence selected from the following amino acid sequences:

```
                                    (SEQ ID NO: 12)
    KKRTLRKNDRKKRGGCPDGAKARC;
    and
                                    (SEQ ID NO: 13)
    KKRTLRKNDRKKRGGCSRRSKSKC.
``` or a modified amino acid sequence from the selected amino acid sequence. The amino acid sequences given in SEQ ID NO: 12 and SEQ ID NO: 13 are amino acid sequences composed of a total of 24 amino acid residues and are constructed by combining the multinucleation-inducing peptide sequence given by SEQ ID NO: 1 or SEQ ID NO: 2 with the amino acid sequence given by SEQ ID NO: 3 and derived from the NoLS of LIM kinase 2, with a linker of 2 glycine (G) residues interposed therebetween.

The herein disclosed multinucleation-inducing synthetic peptide can be readily produced in conformity with common methods of chemical synthesis. For example, a heretofore known solid-phase synthetic method or liquid-phase synthetic method may be used. A solid-phase synthetic method using Boc (t-butyloxycarbonyl) or Fmoc (9-fluorenylmethoxycarbonyl) as the protective group for the amino group is advantageous.

A peptide having the desired amino acid sequence and modifications (C-terminal amidation and so forth) can be synthesized for the herein disclosed multinucleation inducing synthetic peptide using a solid-phase method using a commercially available peptide synthesizer (available, for example, from Intavis AG or Protein Technologies, Inc.)

Or, the multinucleation-inducing synthetic peptide may be biosynthesized based on a genetic engineering procedure. That is, a polynucleotide (typically DNA) is synthesized that has a nucleotide sequence (including the ATG start codon) that encodes the amino acid sequence of the desired multinucleation-inducing synthetic peptide. A recombinant vector is then constructed m conformity with the host cell; this recombinant vector has an expressible gene construct composed of the synthesized polynucleotide (DNA) and various regulatory elements (including a promoter, ribosome binding site, terminator, enhancer, and various cis elements that control the expression level) supporting expression of the amino acid sequence in the host cell.

Using common procedures, this recombinant vector is introduced into a prescribed host cell (for example, yeast, insect cell, and plant cell) and this host cell, or tissue or specimen containing this cell, is cultured under prescribed conditions. By doing this, the target peptide can be expressed and produced within the cell. The peptide is isolated from the host cell (or medium in the case of secretion), and the target multinucleation-inducing synthetic peptide can be obtained by carrying out refolding, purification, and so forth as necessary.

Methods heretofore employed in this field may be used as such for the method for constructing the recombinant vector, the method for introducing the constructed recombinant vector into the host cell, and so forth, and, since these methods are not themselves particular characteristic features of the present invention, a detailed description thereof is omitted.

For example, a fusion protein expression system can be used to bring about the efficient production of large amounts within the host cell. That is, a gene (DNA) encoding the amino acid sequence of the target multinucleation-inducing synthetic peptide is chemically synthesized, and the synthesized gene is introduced into a suitable site in a suitable fusion protein expression vector (for example, glutathione S-transferase (GST) fusion protein expression vectors such as the pET series from Novagen Inc and the pGEX series from Amersham Biosciences). The host cell (typically *E. coli*) is transformed with this vector. The resulting transformant is cultured to produce the target fusion protein. This protein is then extracted and purified. The obtained purified fusion protein is subsequently cleaved with a prescribed enzyme (protease) and the liberated target peptide fragment (the designed multinucleation-inducing synthetic peptide) is recovered using a method such as affinity chromatography. As necessary, refolding is performed using a suitable method. The herein disclosed multinucleation-inducing synthetic peptide can be produced using such a heretofore known fusion protein expression system (for example, the GST/His system from Amersham Biosciences can be used).

Alternatively, a template DNA (i.e., a synthetic gene fragment containing a nucleotide sequence that encodes the amino acid sequence of the multinucleation-inducing synthetic peptide) for a cell-free protein synthesis system is constructed, and, using the various compounds (ATP, RNA polymerase, amino acids, and so forth) required for peptide synthesis, an in vitro synthesis of the target polypeptide can be carried out using what is known as a cell-free protein synthesis system. Reference is made to the reports of Shimizu et al. (Shimizu et al., Nature Biotechnology, 19, 751-755 (2001)) and et al. (Madin et al., Proc. Natl. Acad. Sci. USA, 97(2), 559-564 (2000)) for cell-free protein synthesis systems. At the time of filing of this application, numerous firms were already engaged in contract polypeptide production based on the technology described in these reports; kits for cell-free protein synthesis are also commercially available (fir example, the PROTEIOS (trademark) wheat germ cell fee protein synthesis kit available from CellFree Sciences Co., Ltd. (Japan)).

A single-strand or double-strand polynucleotide containing a nucleotide sequence encoding the herein disclosed multinucleation-inducing synthetic peptide and/or a nucleotide sequence complementary to this sequence can be readily produced (synthesized) by heretofore known methods. Thus, by selecting the codons that correspond to the individual amino acid residues constituting the intended amino acid sequence, a nucleotide sequence corresponding to the amino acid sequence of the multinucleation-inducing synthetic peptide can be easily determined and provided. Once the nucleotide sequence has been determined, a polynucleotide (single strand) corresponding to the desired nucleotide sequence can be readily obtained using, for example, a DNA synthesizer. Then, using the obtained single-strand DNA as a template, the target double-strand DNA can be obtained using various enzymatic synthesis procedures (typically PCR). In addition, the polynucleotide may take the form of DNA or RNA (for example, mRNA). The DNA can be provided in double strand or single strand form. When provided in single strand form, it may be the coding strand (sense strand) or may be the noncoding strand (antisense strand) with a sequence complementary thereto.

As noted above, the thusly obtained polynucleotide can be used as a starting material for the construction of a recombinant gene (expression cassette) for producing the multinucleation-inducing synthetic peptide in various host cells or in a cell-free protein synthesis system.

Insofar as the multinucleation-inducing activity is not impaired, the herein disclosed multinucleation-inducing synthetic peptide may take the form of a salt. For example, an acid-addition salt of the peptide can be used, which can be obtained by an addition reaction according to the usual methods of a commonly used inorganic acid or organic acid. Or, it may take another salt form (for example, a metal salt) insofar as the multinucleation-inducing activity is exhibited. Accordingly, the "peptide" referenced in this Description and in the claims also encompasses peptides in these salt forms.

Insofar as the multinucleation-inducing synthetic peptide effective component can be kept in a state in which its multinucleation-inducing activity is not impaired, the herein disclosed multinucleation-inducing agent may contain any of various (at least one or more types of) pharmaceutically (medicinally) acceptable carriers in correspondence to the form of use. The carriers commonly used in peptide drugs as, e.g., diluents, excipients, and so forth, are preferred. While the carrier can vary as appropriate in correspondence to the application and form of the multinucleation-inducing agent, specific examples are water, physiological buffers, and various organic solvents. It can be an aqueous alcohol (e.g., ethanol) solution of suitable concentration, glycerol, or a nondrying oil such as olive oil. Or it may be a liposome. Examples of secondary components that can be incorporated in the multinucleation-inducing agent are various fillers, extenders, binders, moisturizers, surfactants, colorants, fragrances, and so forth.

There are no particular limitations on the form of the multinucleation-inducing agent. Specific forms can be exemplified by solutions, suspensions, emulsions, aerosols, foams, granules, powders, tablets, capsules, ointments, and aqueous gels. It can also be made as a lyophilizate or granulate for preparation of a drug solution by dissolution in, for example, physiological saline or an appropriate buffer (for example, PBS), immediately before use.

The processes as such that are used to prepare the various drug (composition) forms using the multinucleation-inducing synthetic peptide (main component) and various carriers (secondary component) as starting materials may conform to heretofore known methods, and these formulation methods are not themselves characteristic features of the present invention and a detailed description thereof is thus omitted. A source of detailed information on formulation is, for example, Comprehensive Medicinal Chemistry, edited by Corwin Hansch, Pergamon Press (1990). The contents of this publication are incorporated in their entirety in this Description by reference.

There are no particular limitations on applicable target cells for the herein disclosed multinucleation-inducing agent (multinucleation-inducing synthetic peptide), and multinucleation can be induced (or the induction of multinucleation can be promoted) in eukaryotic cells from various species of organisms. In particular, cells from humans or non-human animals (typically vertebrates and particularly mammals) are preferred as an application target. Viewed from the standpoint of medical utility, tumor cells and particularly malignant tumor cells (cancer cells), for example, squamous cell carcinoma cells and adenocarcinoma cells, are suitable as target cells. Or, viewed from the standpoint of medical utility (particularly from the standpoint of application to regenerative medicine), multinuclear cells (for example, megakaryocytes and osteoclasts) and pre-multinuclear cells prior to multinucleation—for example, megakaryocytes, osteoclasts, precursor cells for megakaryocytes prior to multinucleation (for example, megakaryoblasts prior to multinucleation), precursor cells for osteoclasts prior to multinucleation (osteoclast precursor cells)—are suitable as target cells.

The herein disclosed multinucleation-inducing agent (multinucleation-inducing synthetic peptide) can be used in accordance with a method and dose that correspond to its form and purpose.

For example, when multinucleation is to be induced in a target cell (for example, a tumor cell, multinuclear cell, or pre-multinuclear cell prior to multinucleation) that is being cultured (subcultured) outside the organism (in vitro), an appropriate amount of the herein disclosed multinucleation-inducing agent (that is, multinucleation-inducing synthetic peptide) may be supplied at least once, and at any stage in the culture process (preferably after carrying out culture (proliferation) or subculture for a prescribed period of time), to the medium for the target cultured cell (cell culture) that is to be multinucleated. The cultured cell can be exemplified by established cell lines and primary cell cultures, cellular material that has been temporarily or permanently excised from an organism (cells, living tissue, cell masses, and so forth), and cellular material (including tissue, cell masses, and organs and typically cells) obtained by inducing differentiation from stem cells (for example, iPS cells, ES cells, and hematopoietic stem cells).

The amount of multinucleation-inducing agent (that is, multinucleation-inducing synthetic peptide) supplied and the number of times of supply are not particularly limited because they can vary depending, on conditions such as the type of cultured cell, cell density (cell density at the start of culture), number of passages, culture conditions, type of medium, and so forth. For example, in the case of culture of cells of human origin or non-human animal origin (typically vertebrates and particularly mammals), supply (for example, at the start of culture and with additional supply when the cells are subcultured or when the medium is exchanged) is preferably carried out once to a plurality of times to the cultured cells (cell culture) to provide a multinucleation-inducing synthetic peptide concentration in the medium in the range of about 0.1 μM to 100 μM and preferably in the range from 0.5 μM to 80 μM (for example, 1 μM to 50 μM).

Alternatively, when the induction of multinucleation is carried out on a target cell within an organism (in vivo) (for example, tumor cells, multinuclear cells, or multinuclear cells prior to multinucleation), an appropriate amount of the herein disclosed multinucleation-inducing agent (that is, multinucleation-inducing synthetic peptide) may be converted into a solution and precisely the desired amount may then be administered to a patient (i.e., in vivo) by intravenous, intramuscular, subcutaneous, intradermal, or intraperitoneal injection. Or, a solid form, e.g., a tablet, or a water-based jelly or a gel. e.g., an ointment, can be administered directly or to a tissue of interest (for example, the tumor-affected area or the tissue where the intended cell multinucleation is to be carried out, e.g., the bone marrow or bone) or to the vicinity of this tissue. Oral administration may also be carried out, or administration may be carried out in suppository firm. By doing this, multinucleation can be induced on cells within an organism, typically a tissue of interest or target cells present at its periphery. The amount of administration of the multinucleation-inducing agent (that is, multinucleation-inducing synthetic peptide) and the number of times of its administration are not particularly limited because these can vary with conditions such as the type and location of the target cell in which multinucleation is to be induced.

In addition, the herein disclosed multinucleation-inducing agent (multinucleation-inducing synthetic peptide) can be used in combination with, for example, humoral factors (for example, cytokines and so forth) or a composition (for example, an inhibitor and so forth), in correspondence to the type of target cell and objective.

For example, when multinucleation is to be induced in a tumor cell, the herein disclosed multinucleation-inducing agent (multinucleation-inducing synthetic peptide) may be used with a composition (anticancer agent) that has an additional antitumor effect. This anticancer agent can be exemplified by alkylating agents, antimetabolites, microtubule-targeting agents, platinum agents, anticancer antibiotics, hormone agents, targeted molecular therapy, and so forth.

Or, when multinucleation is to be induced in a multinuclear cell or a pre-multinuclear cell prior to multinucleation, the herein disclosed multinucleation-inducing agent (multinucleation-inducing synthetic peptide) may be used in combination with an additional multinucleation-inducing factor, a differentiation-inducing factor, or a composition that has a multinucleation-inducing effect. When multinucleation is to be induced (promoted) in megakaryocytes (or megakaryocytes prior to multinucleation), the multinucleation-inducing factor can be exemplified by thrombopoietin (TPO), various interleukins (for example, IL-1, IL-3, IL-4, IL-7, IL-11, and so forth), granulocyte macrophage colony-stimulating factor (GM-CSF), erythropoietin (EPO), stem cell factor (SCF), factors belonging to other cytokine families, Rho-associated coiled-coil kinase (ROCK) inhibitors, and histone deacetylase (HDAC) inhibitors. When multinucleation is to be induced (promoted) in an osteoclast (or an osteoclast prior to multinucleation), examples are factors belonging to the tumor necrosis factor (TNF) superfamily, e.g., receptor activator of NF-κB ligand (RANKL); macrophage colony-stimulating factor (M-CSF); factors belonging to the TGF-β superfamily, e.g., TGF-β1; and factors belonging to other cytokine families.

For example, through the administration of the herein disclosed multinucleation-inducing agent (multinucleation-inducing synthetic peptide) so as to supply it to a tumor (cancer)-affected part, the tumor cells can be multinucleated due to the multinucleation-inducing activity thereof and cell division of the tumor cells can be suppressed (inhibited) and cell proliferation by the tumor cells can then be suppressed (inhibited). In other words, the herein disclosed multinucleation-inducing agent can be used as a pharmaceutical composition (antitumor composition, anticancer agent) that can be used to treat tumors (cancer therapy).

For example, through the administration of the herein disclosed multinucleation-inducing agent (multinucleation-inducing synthetic peptide) so as to supply it to a tissue within an organism where multinuclear cells (for example, megakaryocytes, osteoclasts, and so forth) are to be multinucleated, multinucleation can be induced due to its multinucleation-inducing activity in the multinuclear cells (for example, megakaryocytes, osteoclasts, and so forth) and pre-multinuclear cells prior to multinucleation (for example, megakaryoblasts prior to multinucleation, osteoclast precursor cells prior to multinucleation). As a consequence, the functions carried out by the multinuclear cells (for example, megakaryocytes and osteoclasts) in the organism can be reinforced, thus enabling use, for example, as a pharmaceutical composition that contributes to the expression of, for example, an increased platelet production efficiency or regulation of bone metabolism and maintenance of the Ca concentration in the blood.

Or, the induction of multinucleation in a target cell can be efficiently carried out outside the organism (in vitro) by applying a suitable amount of the multinucleation-inducing agent (multinucleation-inducing synthetic peptide) to the target cell (for example, a multinuclear cell or a pre-multinuclear cell prior to multinucleation) and culturing until multinucleation of the target cells has been induced (that is, by the use of the herein disclosed multinucleation induction method). As a consequence, multinuclear cells can be efficiently produced and the number of nuclei in a multinuclear cell can also be increased (promotion of multinucleation). The following, for example, can be used as the target cell here: cellular material that has been temporarily or permanently excised from an organism (living tissue and cell masses, for example, cultured cells) and prescribed cells (including tissues and organs constituted of these cells) obtained by inducing differentiation from stem cells (for example, iPS cells, ES cells, and hematopoietic stem cells) being cultured (subcultured) in vitro.

In addition, by using the herein disclosed multinucleation induction method (an in vitro multinucleation induction method) and/or the multinucleation-inducing synthetic peptide, the time required for the multinucleation of a target cell can be shortened due to the introduction, into tissue in which the cell functions (that is, within the body of a patient), of the target cell that has undergone an efficient induction (promotion) of multinucleation outside the body (in vitro) (that is, a multinuclear cell produced by the herein disclosed art or a multinuclear cell in which the number of nuclei in the cell has been increased).

In addition, the use of a multinuclear cellular material (multinuclear cells or a cell mass or tissue that contains multinuclear cells) that has been produced in large amounts in an in vitro culture system, makes possible the production of cells and biosynthetic products (for example, physiologically active substances such as secreted proteins and hormones) that are produced from these cells. For example, the herein disclosed art can be advantageously used in methods for producing platelets from megakaryocytes. Megakaryocytes that have undergone a satisfactory multinucleation provide a much higher platelet production per cell (several tenfold to several hundredfold) than inadequately multinucleated megakaryocytes, and as a result promoting the multinucleation of megakaryocytes is critical to increasing the amount of platelet production per megakaryocyte cell. As a consequence, platelets can be produced at high efficiencies by using megakaryocytes that have undergone a satisfactory induction of multinucleation using the herein disclosed art. In addition, blood preparations (platelet preparations) can be produced using platelets produced in accordance with the present invention.

Several examples pertaining to the present invention are described below, but this is not meant to imply that the present invention is limited to what is shown in these examples.

Example 1: Peptide Synthesis

A total of three peptides (samples 1 to 3) were produced using the peptide synthesizer described below. The data on the amino acid sequences of these synthetic peptides is listed in Table 1.

TABLE 1

| sample no. | amino acid residues | amino acid sequence total number of |
|---|---|---|
| 1 | KKRTLRKNDRKKR GG CPDGAKARC (SEQ ID NO: 12) | 24 |
| 2 | KKRTLRKNDRKKR GG CSRRSKSKC (SEQ ID NO: 13) | 24 |
| 3 | KKRTLRKNDRKKR (SEQ ID NO: 3) | 13 |

As shown in Table 1, the peptides according to samples 1 and 2 are multinucleation-inducing synthetic peptides that have a multinucleation-inducing synthetic peptide sequence at the C-terminal side of the peptide chain and that at their N-terminal side have an LIM kinase 2-derived amino acid sequence (SEQ ID NO: 3), which is a membrane-permeable peptide sequence, with a linker region of 2 glycine (G) residues interposed therebetween.

That is, the peptide (SEQ ID NO: 12) of sample 1 is a peptide that has a total of 24 amino acid residues and that has the amino acid sequence given by SEQ ID NO: 1 as the multinucleation-inducing synthetic peptide sequence.

The peptide (SEQ ID NO: 13) of sample 2 is a peptide that has a total of 24 amino acid residues and that has the amino acid sequence given by SEQ ID NO: 2 as the multinucleation-inducing synthetic peptide sequence.

As shown in Table 1, the peptide of sample 3 is a peptide that has a total of 13 amino acid residues and that is composed of only an amino acid sequence (SEQ ID NO: 3) derived from LIM kinase 2, which is a membrane-permeable peptide sequence.

The synthetic peptides of samples 1 to 3 were linear peptides, and these synthetic peptides were synthesized by a solid-phase synthesis method (Fmoc method) using a commercial peptide synthesizer (Intavis AG) in accordance with its manual. The mode of use of the peptide synthesizer is not itself a characteristic feature of the present invention and a detailed description thereof is thus omitted.

The synthesized peptides of samples 1 to 3 were dissolved in PBS (−) or DMSO to prepare peptide stock solutions.

Example 2: Evaluation Test 1 of the Multinucleation-Inducing Activity of the Synthetic Peptides for Tumor Cells To evaluate the multinucleation-inducing activity of the multinucleation-inducing synthetic peptides (sample 1 and sample 2) obtained in Example 1, cytoimmunostaining (fluorescence immunostaining) was performed using calreticulin as the cytoplasm marker and nuclear staining was performed with DAPI (4′,6-diamidino-2-phenylindole). HeLa S3 cells (ATCC (registered trademark), CCL2.2), a cultured cell strain originating from human cervical cancer, were used as the sample cells. The evaluation test is described in the following.

HeLa S3 cells were seeded into each well of a 4-chamber (well) cell culture slide (also referred to as a chamber) to provide approximately $1 \times 10^3$ cells per well and were cultured overnight in an incubator under conditions of 5% $CO_2$ and 37° C. The medium used was a common DMEM medium, i.e., DMEM (Wako Pure Chemical Industries, Ltd., Cat. No. 043-30085) containing 10% PBS, 100 units/mL of penicillin, and 100 µg/mL of streptomycin. After this overnight culture, the medium in the culture chamber was exchanged for medium obtained by the addition, to the aforementioned DMEM medium containing PBS, penicillin and streptomycin, of the sample 1, sample 2, or sample 3 peptide in an amount providing a peptide concentration of 50 µM, and subculturing was carried out by culture for 4 days under the same conditions. The control group was a peptide-free group in which only PBS (−) was added in the same volume as the peptide stock solution that was added in the sample addition groups.

After completion of the culture period, the status of multinucleation in the cells in each test group was observed using the following cytoimmunostaining.

The cells in each test group wore first fixed followed by a blocking treatment. Specifically, the medium in the culture chamber in the test group was first removed and washing was carried out twice with cold PBS (−). A solution prepared by mixing 1 volume of methanol with 1 volume of acetone (methanol/acetone=1:1 solution) was then added and the HeLa S3 cells were fixed by standing for 15 minutes on ice. The methanol/acetone=1:1 solution was then removed acid washing was carried out three times with cold PBS PBS (−) containing 3% BSA (PBS (−) that contained 3% BSA) was added and a blocking treatment was carried out for 1 hour at room temperature. After the passage of the prescribed period of time, the PBS (−) containing 3% BSA was removed and washing with cold PBS (−) was performed three times.

Cytoimmunostaining against calreticulin was then carried out using anti-calreticulin antibody and a secondary antibody that recognized the anti-calreticulin antibody. First, a primary antibody dilution—prepared by diluting an anti-calreticulin monoclonal [FMC75] antibody (murine origin, Abcam plc, Cat. No. ab22683) 400-fold with 1% BSA/PBS (−) (PBS (−) containing 1% BSA)—was added to the culture chamber for the HeLa S3 cells and standing overnight (approximately 16 to 18 hours) was carried out at 4° C. After the passage of the prescribed period of time, the primary antibody dilution was removed and washing was performed six times with cold 0.1% BSA/PBS (−) (PBS (−) containing 0.1% BSA). This was followed by the addition, as a secondary antibody, of a secondary antibody dilution—prepared by the 200-fold dilution with 1% BSA/PBS (−) of anti-mouse IgG antibody (goat, product of Life Technologies Corporation, A11029) labeled with fluorescent dye (Alexa (registered trademark) 488)—followed by standing for 2 hours at room temperature. After the passage of the prescribed period of time, the secondary antibody dilution was removed and washing was performed six times with cold 0.1% BSA/PBS (−).

The cells in each test group that had been subjected to this cytoimmunostaining were mounted using a cover glass and Slow Fade (Life Technologies Corporation, Cat. No. S36936), which is a DAPI-containing mountant, and fluorescence observation was performed using a confocal laser microscope.

Figure 1:
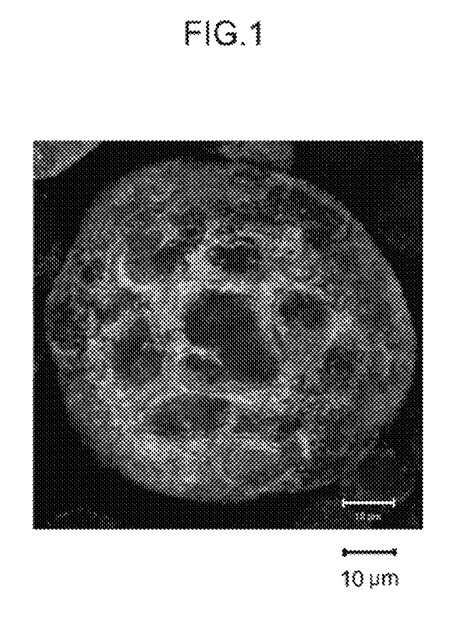
FIG. 1 is a fluorescent micrograph (image) showing the status of HeLa S3 cells after culture under the addition to a HeLa S3 cell culture of a multinucleation-inducing synthetic peptide (sample 1) according to an example; the image was generated by stacking (merging) a DAPI nuclear staining image and a fluorescent image showing the results from cytoimmunostaining using anti-calreticulin antibody.
Figure 2:
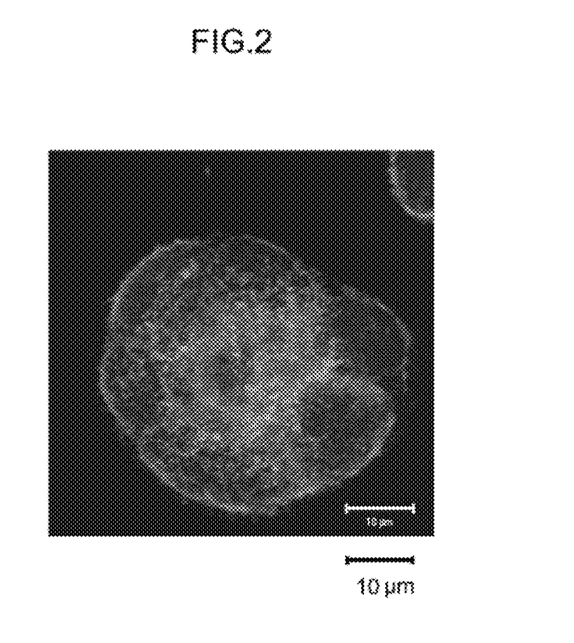
FIG. 2 is a fluorescent micrograph (image) showing the status of HeLa S3 cells after culture under the addition to a HeLa S3 cell culture of a multinucleation-inducing synthetic peptide (sample 2) according to an example; the image was generated by stacking (merging) a DAPI nuclear staining image and a fluorescent image showing the results from cytoimmunostaining using anti-calreticulin antibody.
Figure 3:
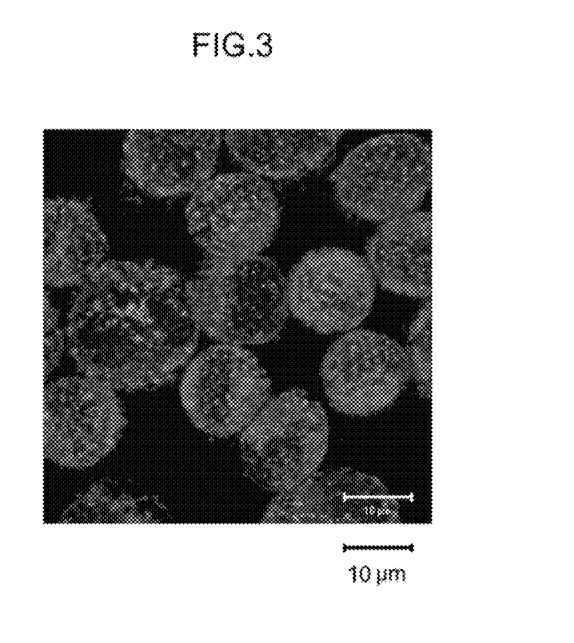
FIG. 3 is a fluorescent micrograph (image) showing the status of HeLa S3 cells after culture under the addition to a HeLa S3 cell culture of a synthetic peptide (sample 3) constructed as a comparative example of only an amino acid sequence constituting a membrane-permeable peptide sequence; the image was generated by stacking (merging) a DAPI nuclear staining image and a fluorescent image showing the results from cytoimmunostaining using anti-calreticulin antibody.
Figure 4:
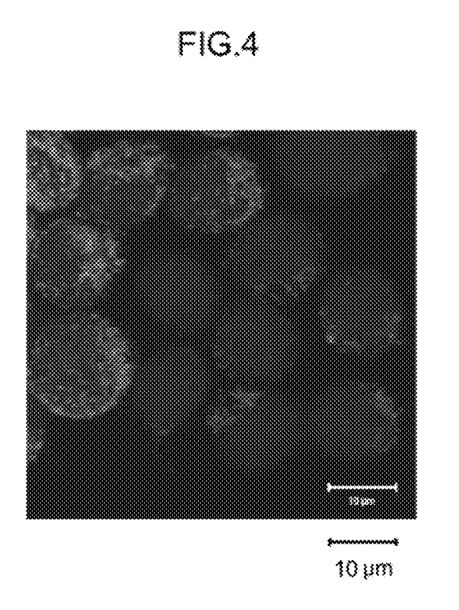
FIG. 4 is a fluorescent micrograph (image) showing the status of HeLa S3 cells after culture without the addition to a HeLa S3 cell culture of the multinucleation-inducing synthetic peptide; the image was generated by stacking (merging) a DAPI nuclear staining image and a fluorescent image showing the results from cytoimmunostaining using anti-calreticulin antibody.

The results of fluorescence observation with the confocal laser microscope are given in FIG. 1 to 4. These images are fluorescence micrographs showing the state of multinucleation of the cells in each test group, and are images obtained by stacking (merging) the DAPI nuclear staining image with the fluorescence image showing the result of probing the state of calreticulin expression by the aforementioned immunofluorescent antibody method. FIGS. 1 to 3 show the results for the groups in which sample 1, sample 2, or sample 3 was added in correspondence to the figure number. FIG. 4 shows the results for the peptide free group.

As shown in the fluorescence microscopic images of the HeLa S3 cells to which the synthetic peptide according to sample 1 or sample 2 (multinucleation-inducing synthetic peptides) had been added (FIG. 1 for the sample 1 addition group, FIG. 2 for the sample 2 addition group), according to the results of the evaluation tests cells in which a plurality of nuclei had formed were observed for the sample 1 addition group and the sample 2 addition group. In contrast to this, cells in which a plurality of nuclei had formed were not observed for the HeLa S3 cells in the sample 3 addition group or in the peptide-free group (FIG. 3 for the sample 3 addition group, FIG. 4 for the peptide-free group). That is, the synthetic peptides of sample 1 and sample 2 were found to induce multinucleation in HeLa S3 cells. These results demonstrate that the herein disclosed multinucleation-inducing synthetic peptide (that is, the multinucleation-inducing agent containing this peptide was able to induce multinucleation in eukaryotic cells (for example, tumor cells of human origin). It was observed that the multinucleated cells of the sample 1 addition group included cells that had a significantly larger number of nuclei per cell than some of the multinucleated cells obtained for the sample 2 addition group.

Example 3: Evaluation Test 2 of the Multinucleation-Inducing Activity of the Synthetic Peptides for Tumor Cells The multinucleation induction ratio was determined for the multinucleation-inducing synthetic peptides (sample 1 and sample 2) obtained in Example 1. The same HeLa S3 cells as in Example 2 were used for the sample cells. The evaluation test is described in the following.

HeLa S3 cells were seeded into each well of an 8-chamber (well) cell culture slide (also referred to as a chamber) to provide approximately $0.5 \times 10^3$ cells per well and were cultured overnight in an incubator under conditions of 5% $CO_2$ and 37° C. The medium used was a common DMEM medium, i.e., DMEM (Wako Pure Chemical industries, Ltd., Cat. No. 043-30085) containing 10% FBS, 100 units/mL of penicillin, and 100 µg/mL of streptomycin. After this overnight culture, the medium in the culture chamber was exchanged for medium obtained by the addition of sample 1 or sample 2 in an amount giving a peptide concentration of 50 µM to DMEM medium prepared by adding 3% FBS, 100 units/mL of penicillin, and 100 µg/mL of streptomycin to the aforementioned DMEM, and subculturing was carried out by culture for 4 days under the same conditions. The control group was a peptide-free group in which only PBS (−) was added in the same volume as the peptide stock solution that was added in the sample addition groups.

After completion of the culture period, the cells in the test groups were subjected to cytoimmunostaining of a cytoplasm marker (calreticulin) nuclear staining as in Example 2. After the execution of the cytoimmunostaining and nuclear staining, the cells each test group were subjected to fluorescence observation using a confocal laser microscope and, for the cells observed in 1 field of vision, the total number of cells and the number of cells presenting two or more nuclei (number of multinucleated cells) were counted. The multinucleation induction ratio (proportion (%) for the number of cells having two or more nuclei with reference to the total number of cells observed in 1 field of vision in the microscopic observation) was calculated using the following formula: multinucleation induction ratio (%)=(number of cells having two or more nuclei)÷(total number of cells)× 100. Using these conditions air the evaluation test for the multinucleation induction ratio, the test was carried out independently three times and the average multinucleation induction ratio was calculated by taking the average of the multinucleation induction ratios obtained in the individual tests. The results are reported in Table 2.

TABLE 2

| sample | total number of cells (number) | number of multinuclear cells (number) | multinucleation induction ratio (%) | average multinucleation induction ratio (%) |
|---|---|---|---|---|
| 1 | 28 | 11 | 39.3 | 40.9 |
|   | 31 | 13 | 41.9 |   |
|   | 29 | 12 | 41.4 |   |
| 2 | 30 | 9 | 30.0 | 35.6 |
|   | 32 | 12 | 37.5 |   |
|   | 28 | 11 | 39.3 |   |
| no peptide addition | 28 | 0 | 0 | 0 |
|   | 30 | 0 | 0 |   |
|   | 31 | 0 | 0 |   |

As shown in Table 2, the multinucleation induction ratios in the sample 1 addition group and the sample 2 addition group were found to be substantially higher than the multinucleation induction ratio (0%) in the peptide-free group. Thus, it was mind that the synthetic peptides of sample 1 and sample 2 (multinucleation-inducing synthetic peptides) could induce multinucleation in not less than at least 30% (typically at least 35%) of the sample tumor cells (human cervical cancer: HeLa S3 cells) within 4 days after supply of the peptide. In other words, the efficiency (multinucleation induction ratio, multinucleation induction probability) of multinucleation induction by the synthetic peptides of sample 1 and sample 2 (multinucleation-inducing synthetic peptides) on the sample tumor cells (HeLa S3 cells) was found to be not less than at least 30% (typically at least 35%). In particular, the sample 1 synthetic peptide was found to have an average multinucleation induction ratio of at least 40% and was thus able to induce multinucleation at a higher efficiency than the sample 2 synthetic peptide (i.e., had a higher multinucleation-inducing activity).

These results demonstrate that the herein disclosed multinucleation-inducing synthetic peptide (i.e., a multinucleation-inducing agent containing this peptide) has a high multinucleation-inducing activity for eukaryotic cells (for example, tumor cells of human origin).

Example 4: Evaluation Test of the Cell Proliferation-Inhibiting Activity of the Synthetic Peptides for Tumor Cells The cell proliferation-inhibiting activity of the multinucleation-inducing synthetic peptides obtained in Example 1 (sample 1 and sample 2) was evaluated by performing an absorbance-based cell proliferation assay (WST-8 assay) using WST-8 (water-soluble tetrazolium salt). The same HeLa S3 cells as in Example 2 were used as the sample cells. The evaluation test is described in the following.

HeLa S3 cells were seeded into each well of a 96-hole (well) plate to provide approximately $5 \times 10^3$ cells per well and were cultured for 6 hours in an incubator under conditions of 5% $CO_2$ and 37° C. The medium used was a common DMEM medium, i.e., the medium contained 10% FBS (HyClone Laboratories, Inc., KSD286623, 100 units/mg of penicillin, and 100 µg/mL of streptomycin in DMEM (Gibco, Product No. 11965-092) containing 2 mM L-glutamine (this medium is also referred to below as the "proliferation assay base medium"), and the amount of medium per well was 100 µL.

After culture for the prescribed period of time, the medium in the culture wells was exchanged for medium obtained by the addition, to the aforementioned proliferation assay base medium, of the sample 1 peptide or sample 2 peptide in an amount providing a peptide concentration of 50 µM. The control group was a peptide-free group in which only PBS (−) was added in the same volume as the peptide stock solution that was added in the sample addition groups.

After this addition of the sample peptide, the 96-hole (well) plate was placed in a $CO_2$ incubator and was cultured at quiescence under conditions of 37° C. and 5% $CO_2$. Using a commercial chromogenic measurement kit (Cell Counting Kit-8, Dojindo Laboratories), the viability of the sample cells (viable cell count) was measured at the time of peptide addition (treatment start time, day 0) and at the point at which 1 day (24 hours) had elapsed after the start of culture in the presence of the peptide (day 1). Thus, utilizing the production of water-soluble formazan due to the reduction of the tetrazolium salt in the reagent by the enzymatic activity of the viable cell, the viable cell count was measured by measuring the amount of water-soluble formazan in the medium using the absorbance (measurement wavelength: 450 nm, reference wavelength: 650 nm). This was performed according to the manual provided with the measurement kit, except for the procedure described in the following.

Specifically, the reagent containing the "water-soluble tetrazolium salt (WST-8)" as the chromogenic substrate was added at 10 µL per well to the cell culture wells after the prescribed culture time had elapsed, followed by incubation for 1 hour under conditions of 5% $CO_2$) and 37° C. The absorbance at a wavelength of 450 nm ($A_{450}$) and the absorbance at a wavelength of 650 nm ($A_{650}$) were then measured on the chromogenic reagent-containing cell culture medium using a spectrophotometer (microplate reader) and the value $A_{450}$-$A_{650}$ of $A_{450}$ corrected by $A_{650}$ was determined. Using 100% for the cell survival rate in the peptide-free group, the cell survival rate (%) for each peptide addition group was calculated using the following formula: cell survival rate (%)={($A_{450}$-$A_{650}$ for the sample addition group on day 1)/($A_{450}$-$A_{650}$ for the sample addition group on day 0)}÷{($A_{450}$-$A_{650}$ for the peptide-free group on day 1)/($A_{450}$-$A_{650}$ for the peptide-free group on day 0)}×100. Using the cell survival rate (%) for the peptide-free group as reference, the reduction n the cell survival rate for each sample addition group was determined to give the cell proliferation inhibition rate (%). That is, the cell proliferation inhibition rate was calculated using the following formula: cell proliferation inhibition rate (%)=100−(cell survival rate of the sample addition group). The results are given in Table 3.

TABLE 3

| sample | cell survival rate (%) | cell proliferation inhibition rate (%) |
|---|---|---|
| 1 | 68.8 | 31.2 |
| 2 | 75.2 | 24.8 |
| no addition | 100.0 | 0.0 |

As shown in Table 3, it was found that cell proliferation was more substantially inhibited in the sample tumor cells (human cervical cancer: HeLa S3 cells) in the sample 1 addition group and sample 2 addition group than for the cells in the peptide-free group. That is, the synthetic peptides (multinucleation-inducing synthetic peptides) of sample 1 and sample 2, through an induction of multinucleation in the sample tumor cells (HeLa S3 cells) in both cases, were found to inhibit cell division in the cells that were multinucleated (multinucleated cells) and as a result were able to stop or suppress tumor cell proliferation.

The cell proliferation inhibition ratio by the synthetic peptides of sample 1 and sample 2 (multinucleation-inducing synthetic peptides) for the sample tumor cell (HeLa S3 cells) was also shown to be not less than at least 20%. In particular, it was shown that the sample 1 synthetic peptide had a cell proliferation inhibition ratio of at least 30% and had a cell proliferation-inhibiting activity higher than that of the sample 2 synthetic peptide.

These results demonstrate that the herein disclosed multinucleation-inducing synthetic peptide i.e., a multinucleation-inducing agent containing this peptide) has a high antitumor activity (tumor cell proliferation-inhibiting activity) on tumor cells (fir example, tumor cells of human origin).

Example 5: Preparation of a Granular Formulation 50 mg of the synthetic peptide according to sample 1 or sample 2 (multinucleation-inducing synthetic peptide) was mixed with 50 mg crystalline cellulose and 400 mg lactose, followed by the addition of 1 mL of an ethanol/water mixed solution and kneading. The kneadate was granulated by a common method to obtain a granular formulation (granular composition) in which the herein disclosed multinucleation-inducing synthetic peptide was the principal component.

INDUSTRIAL APPLICABILITY

As has been described in the preceding, the herein disclosed multinucleation-inducing synthetic peptide has a multinucleation-inducing activity that causes mutt nucleation to occur in a target eukaryotic cell, and as a consequence can be favorably used for the purpose of inducing the multinucleation of a target eukaryotic cell (particularly a cell of human origin). For example, it can be used for the purpose of suppressing the proliferation of tumor cells by inducing the multinucleation of the tumor cells. It can also be used to promote the maturation of megakaryocytes by inducing the multinucleation of megakaryocytes prior to multinucleation (that is, megakaryocyte precursor cells), and thus can be used for the purpose of promoting the production of platelets. Accordingly, the herein disclosed multinucleation-inducing agent can be favorably used, for example, as a composition for application in regenerative medicine and as a composition for application in cancer therapy.

SEQUENCE LISTING FREE TEXT

SEQ ID NOs: 1 to 13 synthetic peptide

The invention claimed is:

1. An artificially synthesized peptide having a multinucleation-inducing activity for at least one type of eukaryotic cell and comprising, in the peptide chain thereof, the following amino acid sequence (A) and amino acid sequence (B):
   (A) an amino acid sequence that constitutes a membrane-permeable peptide sequence; and
   (B) an amino acid sequence given by either CPDGAKARC (SEQ ID NO: 1) or CSRRSKSKC (SEQ ID NO: 2) constituting multinucleation-inducing peptide sequences that have a multinucleation-inducing activity for at least one type of eukaryotic cell, or a modified amino acid sequence formed by conservative substitution of one, two or three amino acid residues in the amino acid sequence and that constitutes a multinucleation-inducing peptide sequence having a multinucleation-inducing activity for at least one type of eukaryotic cell.

2. The peptide according to claim 1, wherein the (A) amino acid sequence that constitutes a membrane-permeable peptide sequence is any amino acid sequence selected from SEQ ID NOs: 3 to 11 or is a modified amino acid sequence formed by conservative substitution of one, two or three amino acid residues in the amino acid sequence and that constitutes a membrane-permeable peptide sequence.

3. The peptide according to claim 1, wherein the (A) amino acid sequence that constitutes a membrane-permeable peptide sequence is the following amino acid sequence:
   KKRTLRKNDRKKR (SEQ ID NO: 3).

4. The peptide according to claim 1, wherein the total number of amino acid residues constituting the peptide chain is not greater than 30.

5. The peptide according to claim 4, comprising either of the following amino acid sequences:

```
                            (SEQ ID NO: 12)
KKRTLRKNDRKKRGGCPDGAKARC;
and
                            (SEQ ID NO: 13)
KKRTLRKNDRKKRGGCSRRSKSKC.
```

6. A composition for inducing multinucleation in at least one type of eukaryotic cell, the composition comprising:
   the peptide according to claim 1; and
   a pharmaceutically acceptable carrier.

7. The composition according to claim 6, wherein the eukaryotic cell is a tumor cell of human origin or non-human mammal origin.

8. A method for inducing multinucleation of at least one type of eukaryotic cell, the method comprising:
   preparing a cell culture that contains the eukaryotic cell;
   supplying the peptide according to claim 1 at least once to the cell culture; and
   culturing the cell culture to which the peptide has been supplied.

9. The method according to claim 8, wherein the eukaryotic cell is a tumor cell of human origin or non-human mammal origin.

\* \* \* \* \*